United States Patent [19]

Hill

[11] Patent Number: 4,671,279
[45] Date of Patent: Jun. 9, 1987

[54] SURGICAL STAPLE APPLYING METHOD

[75] Inventor: William R. Hill, Placerville, Calif.

[73] Assignee: Beta Phase, Inc., Menlo Park, Calif.

[21] Appl. No.: 603,420

[22] Filed: Apr. 24, 1984

[51] Int. Cl.[4] .............................................. A61B 61/04
[52] U.S. Cl. .................................. 128/334 R; 227/19; 128/322
[58] Field of Search ................... 128/334 R, 334, 325, 128/337; 227/19

[56] References Cited

U.S. PATENT DOCUMENTS

| | | | |
|---|---|---|---|
| 2,853,074 | 9/1958 | Olson | 128/334 R |
| 3,144,654 | 8/1964 | Mallina et al. | 128/334 R |
| 4,179,057 | 12/1979 | Becht et al. | 227/19 |
| 4,275,813 | 6/1981 | Noiles | 128/334 R |
| 4,296,881 | 10/1981 | Lee | 128/334 R |
| 4,485,816 | 12/1984 | Krumme | 128/334 R |

Primary Examiner—Gene Mancene
Assistant Examiner—Wenceslao J. Contreras
Attorney, Agent, or Firm—Burns, Doane, Swecker & Mathis

[57] ABSTRACT

Apparatus and method for applying a surgical staple which experiences some spring back following deformation. The invention enables the surgical staple to assume a rectangular shape with the tips thereof positioned together after the staple is closed. Specifically, the staple is deformed to overlap the tips so that release of deforming pressure results in tip-to-tip contact upon spring back. The invention addresses problems relating to skin being interposed between the spaced tips when a staple is closed. Also, as a result of the square-cornered rectangular shape of the closed staple, the problem of rotation of the staple after it is applied to the tissue is impeded. Preferably, the staple is heat recoverable having an open-shape memory configuration.

2 Claims, 13 Drawing Figures

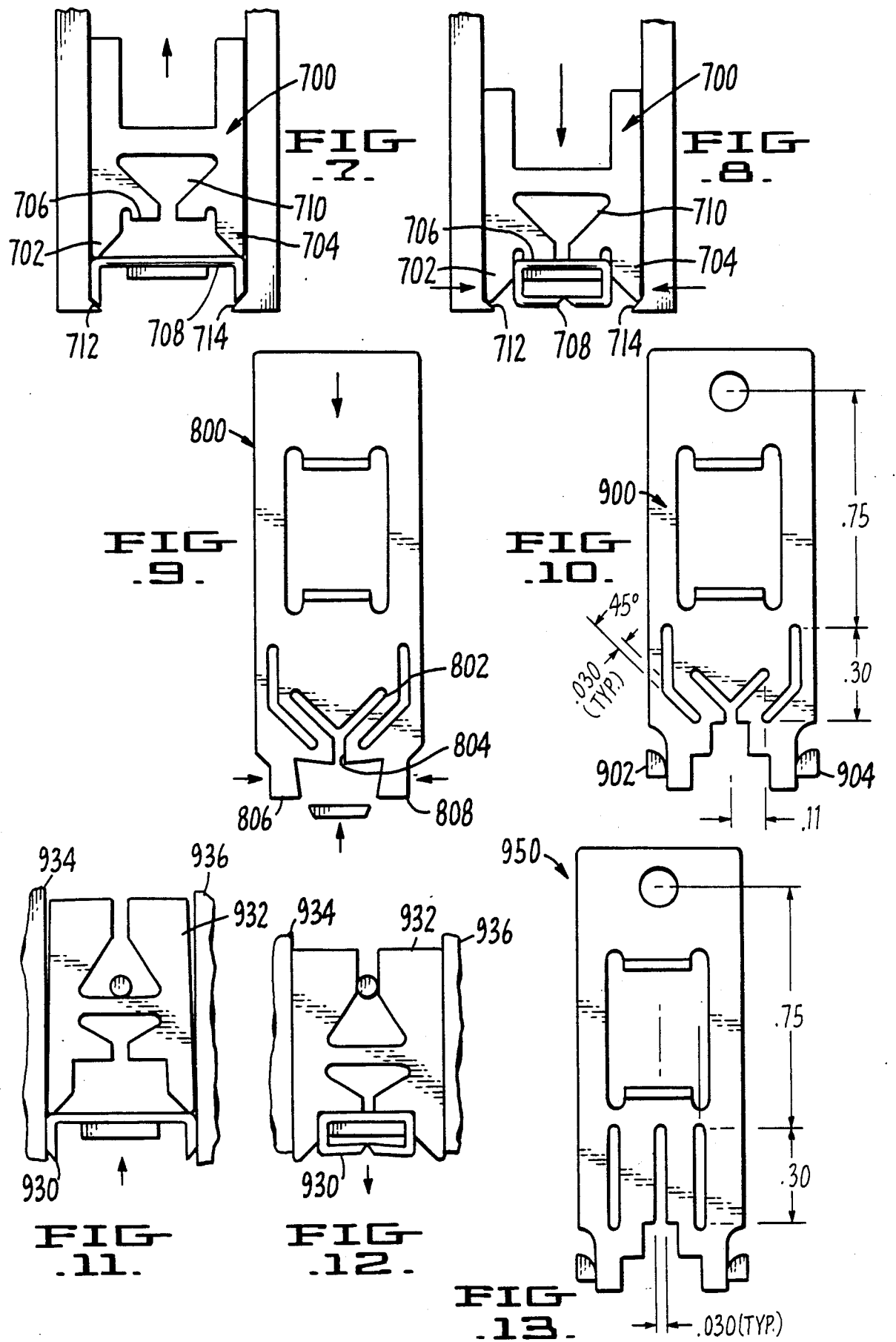

SURGICAL STAPLE APPLYING METHOD

BACKGROUND AND SUMMARY OF THE INVENTION

In the art of surgery, stapling has become popular in ligation and division, anastemoses, resection, and skin and facia closing.

Positive aspects of employing staples include decreasing tissue manipulation and handling, speed of applying the staples, and secure fastening. Accompanying the positive features of surgical stapling, however, are problems that have been recognized.

First, the staple should be easily removed once the stapled tissue heals. In this regard, it is desired that the staple remains secured in position and not reorient itself in the tissue after it is applied. Such reorientation may require the staple to be repositioned before removal can be effectuated, which may result in inconvenience for the surgeon and discomfort for the patient.

In addition, I have found that it is desirable to have the two tips of a staple touching after it is applied for best results. The difficulty in this object is that surgical staples may experience spring back following deformation, resulting in a space between the tips.

To achieve the above objects, I provide a surgical staple formed of a material which is preferably heat recoverable and has a memory shape corresponding to the open position of the staple, the material undergoing some spring back after deformation. When the applied staple is to be removed, heat is transferred thereto and the staple returns from a closed deformed shape to the (open) memory shape.

To insure that the applied staple remains properly positioned for removal, the staple in its closed shape forms a square-cornered rectangular. The square corners prevent reorientation of an applied staple in the tissue.

To achieve the object of tip-to-tip contact, the staple is initially closed to provide tip overlap so that, upon spring back, tip-to-tip contact results.

Hence, according to my invention, a surgical staple is applied in such a way that it maintains its position in tissue, provides tip-to-tip contact without large portions of tissue interposed or pinched between the tips, and in general permits facilitated removal at the proper time.

A conventional stapling device is shown in U.S. Pat. No. 4,179,057. In that patent, one staple after another is advanced to a drive position from which the staples can be ejected in succession by the stapling device into the skin. A review of U.S. Pat. No. 4,179,057 indicates, however, that spring back occurring in the staple shown therein would result in further spreading of the tips and a loss of square corners in the closed staple.

The conventional device discussed above and other devices in the art may be modified by my improvement to enable such devices to effectively apply a staple—preferably a heat recoverable staple—that undergoes spring back after deformation while achieving the aforementioned objects.

BRIEF DESCRIPTION OF THE DRAWINGS

FIG. 7 is a front view of another embodiment of the invention prior to staple driving.

FIG. 8 is a front view of the embodiment shown in FIG. 7 following staple driving.

FIG. 9 is a front view of yet another drive member.

FIG. 10 is a front view of an embodiment similar to that shown in FIG. 9.

FIG. 11 is a front view of another embodiment of the invention prior to staple driving.

FIG. 12 is a front view of the embodiment shown in FIG. 11 following staple driving.

FIG. 13 is a front view of still another drive member in accordance with the invention.

DESCRIPTION OF THE INVENTION

Figure 1:
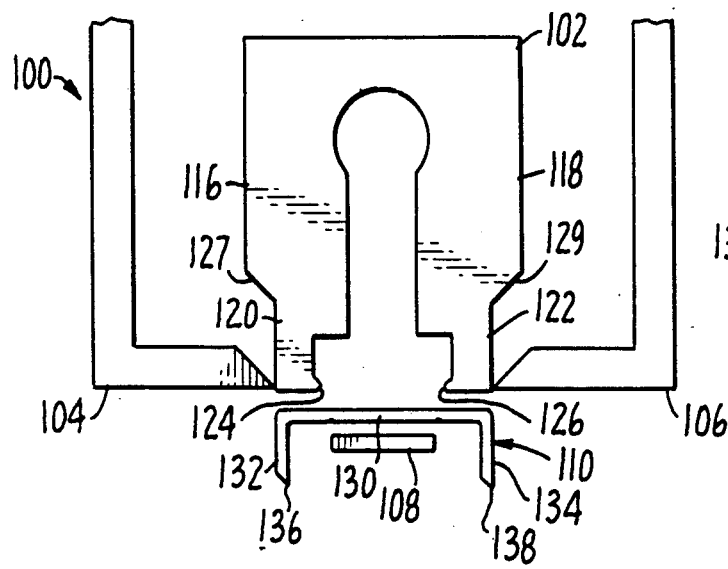
FIG. 1 is a front view of one embodiment of apparatus for applying a staple according to the invention, the apparatus being in a position prior to staple driving.

One embodiment of the present invention is depicted in FIG. 1. That is, the present invention represents an improved surgical staple applier 100 that may be included to modify a conventional surgical stapling device—such as that illustrated in U.S. Pat. No. 4,179,057. Preferably, the invention improves surgical staple devices produced by Ethicon, Incorporated of Somerville, N.J. Specifically, it is contemplated that the staple applier 100 be dimensioned for inclusion in any of the following Ethicon surgical stapling devices.

In FIG. 1, the staple applier 100 is shown including a drive member 102, guide members 104 and 106, and an anvil 108. A staple 110 that is to be applied is also shown.

The guide members 104 and 106 flank the drive member 102. As is conventional, the applier 100 includes a mechanism (not shown in detail) by which a surgeon or other operator can easily move the drive member 102 against the staple 110. The applier 100 also preferably includes a conventional mechanism for feeding one of a plurality of staples after another to be applied to tissue. Such mechanisms which are well-known are not elaborated here.

Referring again to FIG. 1, the drive member 102 is shown as a bifurcated structure that includes two elongated side members 116 and 118 that terminate in respective feet 120 and 122. The inner surfaces of the feet 120 and 122 (which face each other) include a slight inward ridge 124 and 126, respectively, along the lower portions of the feet 120 and 122. Each side member 116 and 118 has a bevelled outer surface 127 and 129, respectively.

The guide members 104 and 106, as well as the anvil 108, are fixedly mounted to the frame of the device (not shown). The drive member 102 travels toward and away from the anvil 108 under the control of the surgeon or operator.

In FIG. 1, the drive member 102 is in a retracted position. The staple 110, which is formed of a material that undergoes spring-back following deformation, is shown having a top bar 130 and two legs 132 and 134. The two legs 132 and 134 extend from the top 130 at right angles and lie in a common plane. The tips 136 and 138 are complementarily tapered—the tip 136 tapering inward from the outer surface thereof and the tip 138 tapering outward from the inner surface thereof.

The staple 110 is formed of a body compatible material, preferably a shape memory metal such as a nickel titanium alloy. The characteristics of such alloys are well known. Briefly, shape memory metals are raised to a first temperature, e.g. 900° C., at which the material is configured into a memory shape. The material is then lowered in temperature, the material being deformable at such low temperatures. Upon raising the material to a second, transition temperature—below the first temperature—the material acts to recover or return to the memory shape.

Shape memory metals, such as nickel titanium alloys or more specifically, 55-Nitinol, typically exhibit some elasticity when deformed from the memory shape. That is, such metals undergo some spring back when released following deformation.

Figure 2:
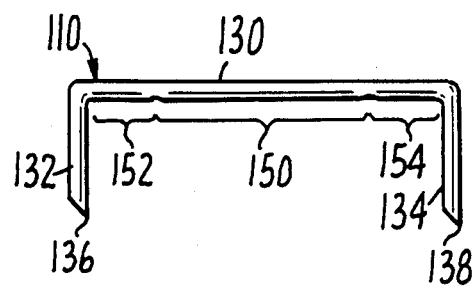
FIG. 2 is a front view of a staple.

The structure of the staple 110 is detailed in FIG. 2. Specifically, the staple 110 includes a midlength 150 positioned between two sidelengths 152 and 154 of the top bar 130. The midlength 150 extends a distance substantially equal to the dimension of the upper surface of the anvil 108 (of FIG. 1). Side lengths 152 and 154 are shown substantially equal in length. The legs 132 and 134 are also shown of equal length. As described below in FIGS. 3 and 4, the staple 110 is bent to form a right angle where the midlength 150 meets the sidelength 152 and where the midlength 150 meets the sidelength 154. The midlength 150 is shown to be equal in length to the sum of the lengths of the two legs 132 and 134. Accordingly, the staple 110 is restructured from a square-cornered u-shaped cross-section before application to a rectangular square-cornered cross-section after application (see FIG. 5). Alternatively, although not preferably, the legs 132 and 134 may be of different lengths; the total length of the legs 132 and 134 equalling the midlength 150 to still provide the square-cornered rectangular shape. Moreover, the sidelengths 152 and 154 are dimensioned to be longer than the side dimension of the anvil 108 to enable staple bending therearound.

Figure 3:
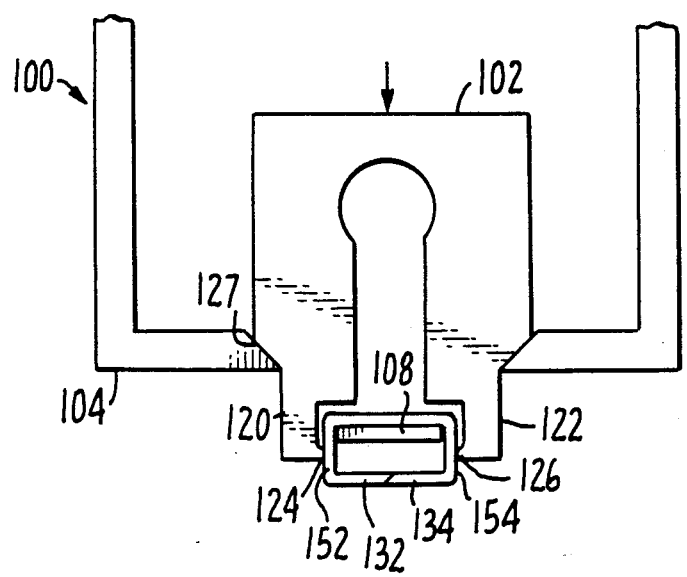
FIG. 3 is a front view of one embodiment of apparatus for applying a staple according to the invention, the apparatus being in a position during staple driving.

Turning to FIG. 3, the drive member 102 is shown driving and bending the staple 110. Feet 120 and 122 have bent the top bar 130 to form the right angles between the midlength 150 and the sidelengths 152 and 154 (see FIG. 2). That is, the feet 120 and 122 bend the staple 110 about the anvil 108 to form the right angles. Between the anvil 108 and walls of the drive member 102, the shaping of the staple 110 is defined.

Figure 4:
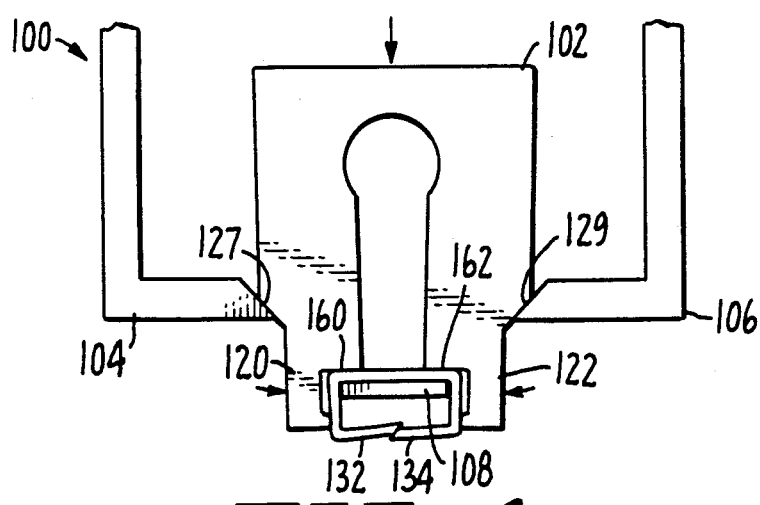
FIG. 4 is a front view of one embodiment of apparatus for applying a staple according to the invention, the apparatus being in a position following staple driving.

In FIG. 4, the drive member 102 has continued its travel. The midlength 150 is positioned between the anvil 108 and lower walls 160 and 162 of the drive member 102. The feet 120 and 122 have been urged toward each other as the bevelled outer surfaces 130 and 132 of the drive member 102 follow inwardly deflected paths determined by the guide members 104 and 106. The effect of this pressing inward is to urge the two legs 132 and 134 to advance beyond tip-to-tip contact into an overlapping position. In FIG. 4, tip 132 overlaps tip 134. The complementary taper of the tips 132 and 134 facilitates this overlapping. Upon withdrawal of the drive member 102 in the direction of the arrow, the staple 110 springs back. The overlap is defined so that upon spring back there is tip-to-tip contact and a square-cornered rectangular shape for the staple 110.

Figure 5:
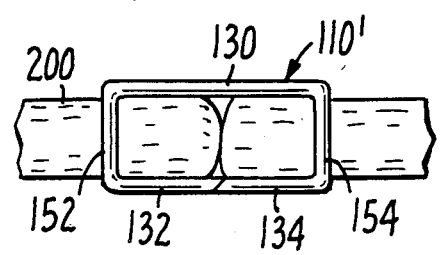
FIG. 5 is a front view of a staple applied by the present invention.

This is illustrated in FIG. 5 where two pieces of tissue 200 and 202 are held together by a staple 110' applied as shown in FIGS. 3 and 4.

Figure 6:
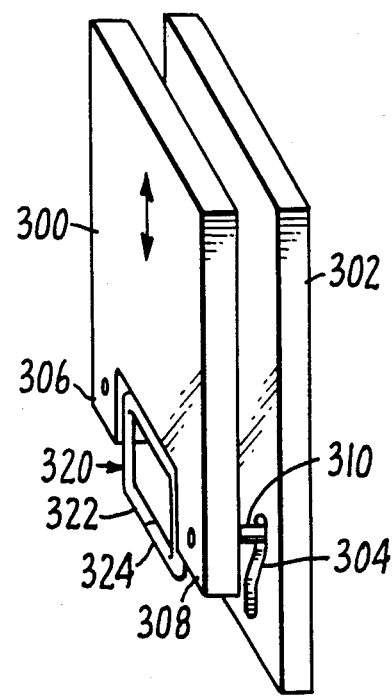
FIG. 6 is an upper front right perspective view of principal elements of an alternative embodiment of the present invention.

FIG. 6 illustrates an alternative structure in accordance with the invention. A drive member 300 is provided in an otherwise conventional surgical stapling device (not shown) to move in the directions shown by the arrows relative to a backplate 302. The backplate 302 includes two slots one of which 304 is shown. Each foot 306 and 308 of the drive member 300 has a respective pin, e.g. pin 310, extending therefrom and into a corresponding one of the slots. For example, pin 310 follows the path defined by slot 304. As depicted in FIG. 6, a staple 320 is bent toward a square-cornered rectangular cross-section until the drive member 300 reaches a certain point along its path. At that point, the two feet 306 and 308 are pressed together thereby urging the legs 322 and 324 of the staple 320 to advance into an overlapping position. In this regard, the feet 306 and 308 are resilient to enable inward flexing and outward return. When the legs 322 and 324 are no longer urged together and are released, the legs 322 and 324 retract to tip-to-tip contact as in FIG. 5.

After the staple 110' has served its purpose and the tissue has healed, the staple 110' is heated to the transition temperature of the staple 110'. The staple 110' returns to its memory shape which corresponds preferably to the open configuration shown in FIGS. 1 and 2.

The drive members 102 and 300 may be formed of any of various plastic or metallic materials, including beryllium copper, which feature resilience or springiness.

Other techniques and structures for urging the legs of an applied staple into an overlapping relationship from which the staple can spring back into a tip-to-tip position may be employed in accordance with the invention. For example, the drive member may comprise a plurality of elements rather than the single bifurcated structure shown.

FIGS. 7 through 13 are alternative embodiments which are readily understood in view of the above teachings. In FIGS. 7 and 8, a drive member 700 is shown having two foot members 702 and 704 and a lower surface 706 which abuts a staple 708. The drive member 700 has a recess 710 extending upward from the lower surface 706, enabling the foot members 702 and 704 to be pressed together by two flanking guide members 712 and 714 as indicated by the arrows.

FIG. 9 shows a drive member 800 provided with a control slot 802 recessed upward from a lower surface 804. The drive member 800 is flexible to enable foot members 806 and 808 to be pressed inwardly against an applied staple.

FIG. 10 shows an embodiment similar to that of FIG. 9. The outer contour of the FIG. 10 drive member 900, however, is curved and contacts curved protruding members 902 and 904 along its travel.

FIGS. 11 and 12 show another embodiment before and after a staple 930 is applied. The drive member 932 travels between guide members 934 and 936.

FIG. 13 shows still another drive member 950 in accordance with the invention.

Other improvements, modifications, and embodiments will become apparent to one of ordinary skill in the art upon review of this disclosure. Such improvements, modifications and embodiments are considered to be within the scope of this invention as defined by the following claims.

I claim:

1. Apparatus for applying a staple that exhibits spring-back following deformation, the apparatus comprising:

an anvil; and a drive member, said drive member capable of movement toward and away from said anvil in a first direction, said drive member also capable of movement toward and away from said anvil in a second direction that is generally perpendicular to said first direction, movement of said drive member in said first direction moving a staple into tissue to be connected, continued movement in said first direction bending a staple to be connected about said anvil, said drive member capable of translating subsequent movement in said first direction into mvoement in said second direction to overbend legs of a staple beyond a tip-to-tip contact to compensate for spring-back.

2. A method of employing a surgical staple comprising the steps of:

providing the staple having a top bar and two legs extending therefrom, the legs having tips at the distal ends thereof, the staple being formed of a material that exhibits some spring-back after deformation;

bending the top bar of said staple at right angles thereto, causing said tips to be generally opposed to each other;

operatively moving said legs and said tips toward each other until said legs are in overlapping position; and discontinuing said movement and removing force from said legs to allow said legs to spring back to a point where said tips are in abutting relationship.

* * * * *

UNITED STATES PATENT AND TRADEMARK OFFICE
CERTIFICATE OF CORRECTION

PATENT NO. : 4,671,279
DATED : June 9, 1987
INVENTOR(S) : William R. Hill

It is certified that error appears in the above-identified patent and that said Letters Patent is hereby corrected as shown below:

Title should be --Surgical Staple Applying Method and Apparatus--

Column 1, line 37, "rectangular" should be --rectangle--.

Column 2, line 36, delete "following".

Column 5, line 19, "mvoement" should be --movement--.

Signed and Sealed this

Twenty-seventh Day of September, 1988

Attest:

DONALD J. QUIGG

*Attesting Officer*  *Commissioner of Patents and Trademarks*